United States Patent [19]

Takahashi et al.

[11] 4,058,736
[45] Nov. 15, 1977

[54] METHOD AND APPARATUS FOR INSPECTING EXTRANEOUS SOLID SUBSTANCES CONTAINED IN LIQUID

[75] Inventors: Toshio Takahashi, Honjo; Toshiyasu Ehara, Misato; Ryosaku Tagaya; Mikio Tagaya, both of Isezaki, all of Japan

[73] Assignee: Eisai Co., Ltd., Tokyo, Japan

[21] Appl. No.: 669,959

[22] Filed: Mar. 23, 1976

[30] Foreign Application Priority Data

Mar. 25, 1975 Japan .................................. 50-34897

[51] Int. Cl.² ............................................. G01N 21/26
[52] U.S. Cl. .................................... 250/573; 250/227; 356/103
[58] Field of Search ............... 250/573, 574, 576, 227; 178/7.6; 350/96 R, 96 B; 356/103, 104

[56] References Cited

U.S. PATENT DOCUMENTS

| | | | |
|---|---|---|---|
| 3,238,294 | 3/1966 | Krauss | 178/7.6 |
| 3,240,106 | 3/1966 | Hicks | 250/227 |
| 3,325,594 | 6/1967 | Goldhammer et al. | 250/227 |
| 3,627,423 | 12/1971 | Knapp et al. | 250/573 |
| 3,800,149 | 3/1974 | Lang | 250/227 |

Primary Examiner—David C. Nelms
Attorney, Agent, or Firm—Wenderoth, Lind & Ponack

[57] ABSTRACT

An improved method for inspection of extraneous substances which may exist in a transparent liquid filled in a transparent container such as an ampoule which comprises rotating the container, projecting light through the liquid in the container, measuring the intensity of light beams passed through the container, and determining the extent of interception of light due to the presence of the substances. The invention is characterized by providing two rotating scan heads on an optical fiber line-circle converter and connecting two photoelectrical elements to the heads. This achieves, with the conventional speed, essentially the same effect as that obtained by doubling the rotating speed of the scan heads.

8 Claims, 4 Drawing Figures

METHOD AND APPARATUS FOR INSPECTING EXTRANEOUS SOLID SUBSTANCES CONTAINED IN LIQUID

This invention relates to a method and apparatus for inspecting for extraneous solid substances that may exist in a transparent container filled with a transparent fluid.

BACKGROUND OF THE INVENTION

There are known and used various type methods for inspecting liquid by employing a photoelectrical element besides the macroscopic inspecting methods for checking and determining the presence of extraneous or alien solid substances which may exist in admixture, for example, in medical liquids, liquid food and drink, cosmetics, liquid chemicals and reagents in the liquid state contained in a transparent container, for example, an ampoule, a vial, bottles or other kinds of containers.

This invention is concerned with the improvement of the type of method wherein the intensity of light passed through the liquid to be inspected is measured, and more particularly to a method which a container such as ampoule is illuminated and then a photoelectric element measures the extent of interception of light beams due to extraneous substances which may exist in the liquid in the container. The photoelectric element receives the light beams which penetrates through the liquid in the container without interception when no extraneous substance exists in the liquid. However, when extraneous substances do exist in the liquid part of the light beams are intercepted by the extraneous substance, and there is a decrease in the amount of the light reaching the photoelectric element. Thus, the amount of the extraneous substance in the liquid can be determined by measuring of the decrease in light.

Generally speaking, the higher the rotating speed of a rotating scan head on an optical fiber line-circle converter used in the above-mentioned system in which the light beams are passed through the liquid is measured, the more the performance of the system for detecting the extraneous solid substance is enhanced, because, due to the random motion of the extraneous substance, the higher the speed of operation or rotation, the higher the probability of detection. (However, an increased rotating speed in excess of about 5000 r.p.m. caused difficulty in mechanical structure.)

SUMMARY OF THE INVENTION

An object of this invention is to provide a method and an apparatus which make it possible to detect precisely the extraneous substances which are floated in a special motion in the liquid. According to this invention, there is achieved, by the use of two rotating scan heads, essentially the same effect as that obtained by increasing the rotating speed of the scan as might be obtained by doubling the rotating speed of a single scan conventional.

This invention pertains to a method for determining the presence of extraneous solid substances which may exist in transparent liquids by interception of light due to the existence of the substance. In this method, a rotating sealed transparent container filled with a transparent liquid causes rotation of the extraneous solid substance in the liquid. Light is projected through the liquid in the container, and the intensity of light beam passed through the container is measured. The method is characterized by providing two rotating scan heads aligned coaxially on a central axis of an by optical fiber line-circle converter, and connecting two photoelectrical elements to the heads, respectively.

The other object of this invention is to provide a method and an apparatus which keeps the two rotating scan heads on the optical fiber line-circle converters in balance, so that high speed rotation may be attained. To achieve this, the two rotating scan heads are placed at symmetric positions on the circular end of the optical fiber line-circle converter.

A further object of this invention is to provide a reasonable design from apparatus fitting the mechanical adaptation of the method. Thus, the apparatus comprises placing the shaft parts of two rotating scan heads in an opposite direction to each on the central axis of the converter and connecting photoelectric elements to each of out-put terminals. Alternatively, the apparatus is provided by optically connecting the respective rotating parts (i.e. shaft parts and in-put terminals) of two rotating scan heads with optical fibers in the axis of rotation by way of a reflecter.

A single rotating scan head has been used in the conventional method. According to the method of this invention, however, two rotating scan heads are provided, so that the same effect is acquirable as would be obtainable if the rotating speed of the scan head in the conventional apparatus were doubled and thereby enhancing the performance of the system remarkably.

BRIEF DESCRIPTION OF THE DRAWINGS

This invention will be described more in detail with reference to the accompanying drawings which illustrate the preferred embodiments.

DETAILED DESCRIPTION OF THE INVENTION

Figure 1:
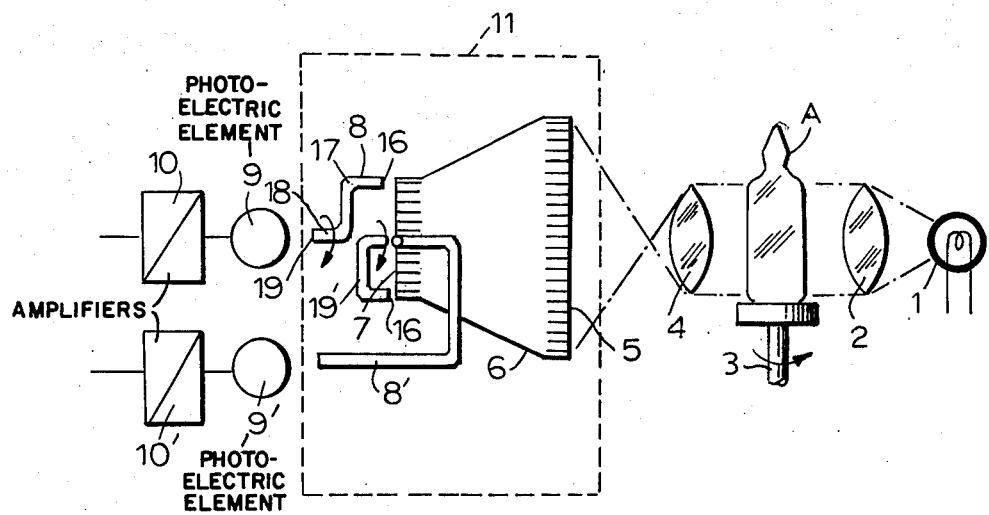
FIG. 1 is a schematic diagram of the arrangement of an apparatus of the present invention.

Referring to FIG. 1 a light beam from a light source 1 is collimated by a condenser lens 2 disposed in front of the source and illuminates an ampoule (A) to be inspected. This ampoule is fixedly supported on a rotating turntable 3. The rotating turntable 3 is rotated at high speed and is then stopped suddenly. However, both the liquid in the ampoule and any extraneous substance mingling in the liquid continue to be rotated due to inertia. An image lens 4 focuses the image of the extraneous substance on the linear end 5 of optical fibers 6 in an optical fiber system scanner, so that the image of the extraneous substance prevents the light beam from the lamp 1 from reaching the light-receiving surface of the optical fiber i.e. the linear end of the fibers. The darkness (i.e. the image of the extraneous substance) on the linear end is transmitted to the circular end 7 through the optical fibers as is well as brightness on the linear end (when no extraneous material is present). The dark or bright state of the circular end 7 is picked up by two rotating scan heads 8 and 8' and is transmitted therethrough to the light-receiving surface of two photoelectrical elements 9 and 9' where it is converted into electric pulse signals which are amplified in amplifiers 10 and 10'.

Each of the rotating scan heads 8 or 8' is made of optical fiber and consists of an in-put end or terminal 16 or 16', an arm part 17 or 17', a shaft part 18 or 18', and an out-put end or terminal 19 or 19', respectively.

Thus, the presence of the extraneous solid substance is converted into an electric pulse signal, whereby it is possible to determine whether or not an extraneous solid substance exists in the liquid of the ampoule.

In the optical fiber system scanner, an optical fiber line-circle converter is constituted by a plurality of optical fibers which each have respective by a minute light-receiving surface and which together are arranged to form a line. Each optical fiber has a cross-sectional dimension corresponding to the dimension of the minimum extraneous substance to be inspected (precisely, to the dimension of the image of the minimum substance to be inspected). Each light-receiving surface is scanned in turn.

Figure 2:
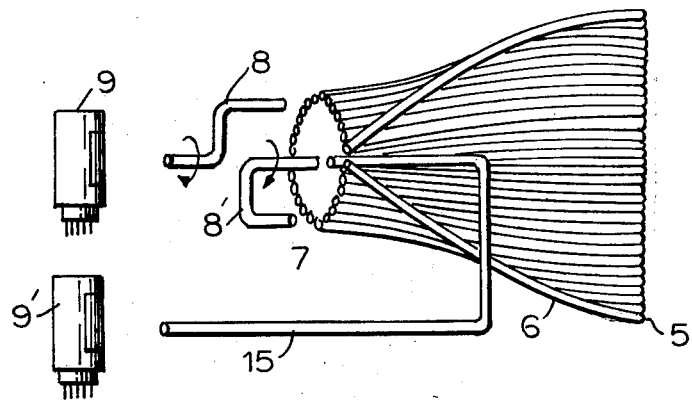
FIG. 2 is an enlarged, perspective view of an optical fiber line-circle converter capable of being used as a scanning device in FIG. 1.

An example of the scanning device will be described. Referring to FIG. 2 which illustrates an enlarged, perspective view of the optical fiber line-circle converter, the optical fiber system scanning device 11 is constituted by a line-circle converter using a plurality of optical fibers 6 each having a diameter of 100μ, rotating scan heads 8 and 8' and photoelectrical elements 9 and 9'. The optical fibers together form, at one end, a linear end 5 in the direction parellel to the longitudinal direction of the ampoule and form, at the other end, a circular end 7 (thus the fibers constitute a line-circle converter structure).

Respective in-put ends 16 and 16' of the rotating scan heads 8 and 8' are adapted to run along the circular end 7 and to scan it. The out-put ends 19 and 19' of the heads 8 and 8' are optically connected to the light-receiving surfaces of the photoelectrical elements 9 and 9', respectively. However, the head 8' is optically connected through an optical fiber 15 to the element 9'. Each individual light-receiving surface on the linear end 5 of these optical fibers is illuminated to be considerably brightened by the light beams from the light source passing through the ampoule which has been rotated at a high speed and suddenly stopped.

However, when the image of the extraneous substance momentarily runs across one or more light-receiving surfaces of the linear end 5 (i.e. one or more endface of optical fibers), the light-receiving surfaces of the optical fibers are darkened because the extraneous substance prevents the light beam from the light source from reaching the light-receiving surface. The optical fibers 6 transmit the brightness or darkness on the linear end 5 to the circular end 7, and the rotating scan heads are rotated along the circular end 7 to pick up this bright or dark condition on each optical fiber endface at the circular end 7. Then, the photoelectrical elements convert the state into the amount of electric current. Thereafter, by a well known method, the specimens are divided according to this electrical signal into a group of specimens with an extraneous substance and a group of specimens without it.

In-put ends 16 and 16' of the two rotating scan heads 8 and 8' are optically connected to the circular end 7 of the optical fiber line-circle converter and the shaft parts 18 and 18' are placed on a rotating shaft 12 having a common center axis in an opposit direction to each other. Each of out-put ends 19 and 19' is connected to a photoelectric element respectively. The arm parts 17 and 17' may be directed in an arbitary angle, but it is preferable that it be 180° from each other and the two in-put ends 16 and 16' are optically connected to the circular end 7 of the optical fibers 6 at two symmetrical positions around the circle so that a good balance is kept and a high speed of rotation may be aquired. However, it should be noted that the angle is not limited to 180° in this invention.

Figure 3A:
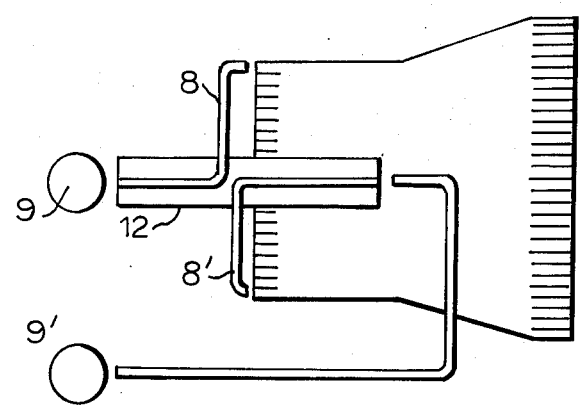
FIGS. 3a and 3b are longitudinal sectional views of rotating scan heads in accordance with preferred embodiments respectively.
Figure 3B:
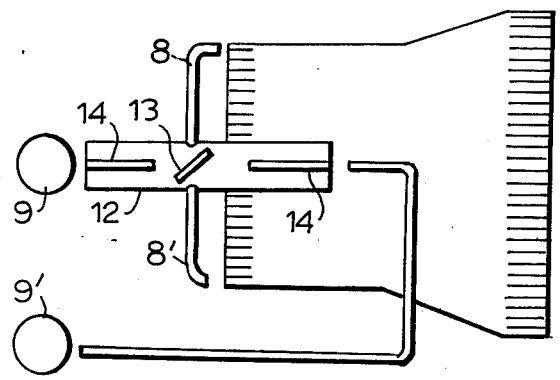

FIGS. 3a and 3b show two embodiments of rotating scan heads, respectively. In FIG. 3a, the shaft parts of the rotating scan heads 8 and 8' are fixed to a rotating scan shaft 12 positioned on a common axis with rotation of the heads 8 and 8', respectively. In FIG. 3b, the rotating scan heads 8 and 8' are optically connected to optical fibers 14 and 14' by way of a reflector 13 such as a mirror, a prism and the like, with both reflecting surfaces, respectively, and fixedly supported on a rotating scan shaft 12 located on common axis of rotation of the heads.

According to this invention, a high accuracy of inspection is attainable even if the extraneous substance is of lower reflectance, because the fact that the extraneous substance prevents arrival of light beams at the light-receiving surfaces of the optical fibers is used for inspection to thereby obtain signals with an increased S/N ratio. Further, the use of two rotating scan heads serves to reasonably detect any extraneous substance which is floating in a special motion provides essentially the same effect as that obtained by increasing doubling the rotating speed of the scan head while the speed is kept as conventionally employed; and enables a good balance of the rotating scan heads and a reasonable design fitting for the mechanical aptitude.

Because the minimum diameter of such optical fibers is the minimum diameter of the extraneous substance to be detected, the minimum dimension of the extraneous substance to be detected may be optionally varied or selected by an adjustment of the magnification of the image lens. The light-receiving surfaces of the optical fibers may be arranged to form two or more lines in parallel with each other.

What is claimed is:

1. A method for determining the presence of extraneous solid substances in a liquid container in a transparent container comprising:
   rotating said container, thereby causing said liquid and said extraneous substances therein to rotate;
   stopping rotation of said container;
   projecting light through said stopped container;
   receiving said light projecting through said stopped container which is not blocked by solid substances in said liquid in the line end of an optical fiber line-circle converter and allowing said light to transmit through said optical fibers of said converter to the circle end thereof;
   detecting the light transmitted to the circle end of said converter with a plurality of rotating scan heads spaced from and rotating about said circle end on at least one shaft coaxially mounted through the axial center of the circle end of said optic converter; and
   optically connecting each of said scan heads to individual photoelectric members.

2. A method as claimed in claim 1 wherein two photoelectric members are provided and two scan heads having two aligned shafts are provided, said aligned shafts projecting longitudinally in opposite directions along the central axis through said circle end and optically connecting said scan heads to said photoelectric members respectively.

3. A method as claimed in claim 1 wherein two shaft-mounted scan heads are provided and have their input ends spaced from said optical fibers in said converter in a symmetrical configuration about the axial center of the circle end of said converter.

4. A method as claimed in claim 1 wherein two shaft-mounted scan heads are provided and reflecting means is provided for reflecting and optically transferring the light received by said scan heads to said photoelectric members.

5. An apparatus for determining the presence of extraneous solid substances in a liquid in a transparent container, said apparatus comprising:
   a rotatable turntable means for supporting and rotating said container thereon;
   a light source adjacent said turntable means and said container thereon for projecting light rays toward said container;
   a condenser lens between said light source and said container on said turntable means for collimating the light rays from said light source directed toward said container;
   a plurality of photoelectric members;
   scanning means between said turntable and said photoelectric members for receiving the light rays from said light source passing through said container unobstructed by any of said extraneous solid substances and optically transferring said light rays to said photoelectric members, said scanning means comprised of:
   an optical fiber line-circle converter means, the line portion thereof adjacent said container, for receiving said light rays travelling through said container, and
   a plurality of rotating scan heads of optical transfer material rotatable about the circle end of said converter, said scan heads having shaft portions coaxially aligned with the longitudinal axial center of the circle end of said converter, and said scan heads being optically connected to said photoelectric members;
   focusing lens means between said container and the line end of said converter for focusing the light rays passing through said container onto the line end of said converter; and
   amplifying means connected to said photoelectric members for amplifying the output from said photoelectric members.

6. An apparatus as claimed in claim 5 wherein:
   said plurality of scan heads is comprised of a first and a second scan head; said plurality of photoelectric members is comprised of a first photoelectric member and a second photoelectric member;
   said first scan head has a head portion opposite the circle end of said converter and a first shaft portion longitudinally aligned with the axial center of said circle end of said converter and extending toward said first photoelectric member;
   said second scan head has a head portion opposite the circle end of said converter, a second shaft portion longitudinally aligned with the axial center of said circle end of said converter and extending in the direction opposite the longitudinal direction of said first shaft portion, and a third shaft portion spaced from and optically connecting said second shaft portion and said second photoelectric member; and
   said first and second shaft heads are symmetrically positioned around the circumference of the circle end of said converter.

7. An apparatus as claimed in claim 6
   further comprising a rotary shaft longitudinally, axially aligned with the axial center of said circle end of said converter,
   wherein said first scan head is mounted through said rotary shaft, and said first shaft portion is coaxially aligned with the longitudinal axis of said rotary shaft; and
   wherein said second scan head portion and said second shaft portion are mounted through said rotary shaft, said second shaft portion being coaxially aligned with the longitudinal axis of said rotary shaft.

8. An apparatus as claimed in claim 6
   further comprising a rotary shaft longitudinally coaxially aligned with the axial center of the circle end of said converter;
   wherein said plurality of photoelectric members is composed of a first photoelectric member and a second photoelectric member; and
   wherein said plurality of scan heads is comprised of:
   a first scan head mounted through said rotary shaft; said first scan head having a head portion opposite the circle end of said converter and a first shaft portion spaced from said head portion coaxially aligned with the longitudinal axis of said rotary shaft and extending therealong toward said first photoelectric member,
   a second scan head mounted through said rotary shaft having a head portion opposite the circle end of said converter on the side of said rotary shaft opposite said first scan head head portion, a second shaft portion spaced from said head portion coaxially aligned with the longitudinal axis of said rotary shaft and extending in the longitudinal direction opposite said first shaft portion, and a third shaft portion longitudinally aligned with and spaced from said second shaft portion and said rotary shaft optically connecting said second shaft portion and said second photoelectric member, and
   reflecting means between said first scan head head portion and said first shaft portion and between said second scan head head portion and said second shaft portion for reflecting the light passing through said head portions to said shaft portions.

* * * * *